United States Patent [19]
Partenheimer

[11] Patent Number: 4,992,580
[45] Date of Patent: Feb. 12, 1991

[54] PRODUCTION OF POLYCARBOXYLIC ACIDS WITH A MOLYBDENUM-ACTIVATED COBALT CATALYST

[75] Inventor: Walter Partenheimer, Naperville, Ill.

[73] Assignee: Amoco Corporation, Chicago, Ill.

[21] Appl. No.: 782,230

[22] Filed: Sep. 30, 1985

[51] Int. Cl.$^5$ .................... C07C 51/265; C07C 63/26; C07C 63/307; C07C 63/313
[52] U.S. Cl. .................................................... 562/416
[58] Field of Search ....................................... 562/416

[56] References Cited
FOREIGN PATENT DOCUMENTS 2119762 8/1972 France ................................. 562/416
11495 6/1940 Japan .................................. 562/416
19786 6/1972 Japan .................................. 562/416

Primary Examiner—Vivian Garner
Attorney, Agent, or Firm—Gunar J. Blumberg; William H. Magidson; Ralph C. Medhurst

[57] ABSTRACT

The addition of molybdenum to oxidation catalysts provided by a heavy transition metal-bromine ion combination containing cobalt uniquely increases catalytic activity of said combustion for converting methyl groups to the corresponding carboxylic acid groups on the benzene nucleus. Such greater catalytic activity is manifested by higher yields of aromatic acids. The polycarboxylic acids produced by the novel process are useful as raw materials for fibers and films.

8 Claims, No Drawings

PRODUCTION OF POLYCARBOXYLIC ACIDS WITH A MOLYBDENUM-ACTIVATED COBALT CATALYST

BACKGROUND OF THE INVENTION

The possibility of using liquid-phase instead of vapor-phase oxidation for the preparation of benzene carboxylic acids was first indicated by the disclosure in U.S. Pat. No. 2,245,528 of the catalysis provided by transition or variable-valence metals, especially cobalt, in a liquid phase of saturated lower aliphatic acid at temperatures from 100° to 320° C. and pressures to maintain the liquid phase of the aliphatic acid. Such catalysis, according to said patent, was advantageously promoted by the use of a ketone, such as methylethyl ketone, or aldehyde, such as acetaldehyde. Unfortunately, such aldehyde- or ketone-promoted variable-valence metal catalysis was useful only for converting mono-, di-, or trimethylbenzenes to their respective benzene monocarboxylic acids: benzoic, toluic, and dimethylbenzoic acids. Two separate, later, and somewhat parallel lower temperature (80°-100° C.) modifications of the aldehyde- or ketone-promoted cobalt catalysis in a liquid phase of acetic acid did provide commercially feasible conversion of xylenes to phthalic acids, especially p-xylene to terephthalic acid, but only at the expense of using rather high molar concentrations of cobalt and, with respect to p-xylene, rather large quantities of acetaldehyde or methylethyl ketone promoter which were oxidized to acetic acid.

The disadvantages of using high concentrations of cobalt promoted with large quantities of aldehyde or ketone are overcome by my novel process wherein molybdenum is used to activate the cobalt. According to my novel process, the use of molybdenum, cobalt, manganese, and bromine in a ratio of 0.001:1:1:2 to about 0.5:1:1:2 is effective in converting di- or polymethylbenzenes to their corresponding aromatic acids.

For the liquid-phase oxidation of di- and trimethylbenzenes with molecular oxygen, it has been discovered that molybdenum is particularly useful for substantially enhancing the activity of cobalt in a system where cobalt, manganese, and bromine are used as catalysts.

Cobalt is the most expensive component in a cobalt-manganese-bromine catalyst system, approximately ten to fifteen times more expensive than manganese. Therefore, there is great economic incentive to replace or reduce the cobalt component in the oxidation catalyst. My novel process has succeeded in doing just that by activating the cobalt moiety with molybdenum, thus reducing the total amount of cobalt to be used in a polyalkyl oxidation system wherein cobalt is the sole or most active component. A novel feature of molybdenum as a cobalt catalyst activator in the oxidation of polymethylbenzenes to the corresponding polycarboxylic acids is that much less cobalt is required to obtain satisfactory yields. However, the ratio of molybdenum to cobalt has to be in the range of about 0.005 to about 0.5 parts by weight. However, molybdenum is a catalyst poison when the ratio of molybdenum to cobalt exceeds about 0.5 parts by weight. Molybdenum is an effective promoter for the cobalt-manganese-bromine catalyst systems for the oxidation of polymethylbenzenes to the corresponding polycarboxylic acids. The term "activation", as used herein, means the ability of a catalyst component to increase the rate of oxidation of polymethylbenzenes to the corresponding polycarboxylic acids.

The data in Tables 2 through 7 are from a specially designed oxidation reactor in which specific effects on the rate of oxidation can be determined. The reactor operates at a temperature of 95° C. and at atmospheric pressure. At this temperature and pressure the oxidation of alkylaromatic compound is occurring so slowly that the composition of the species being oxidized is essentially constant over the time period of the experiment. Because the composition of the alkylaromatic compound remains constant, so does the rate of oxidation. The effect of water on the rate of oxidation can now be evaluated by adding an increment of water to the reactor. For example, in Table 2 in Example 6, water is added to the reactor. This results in a decrease in the rate of oxidation from 6.66 to 5.64 to 4.33 to 1.43 ml oxygen reacted/min as increasing amounts of water are added. The addition of trimellitic acid has a similar effect (see Example 1). This demonstrates that both water and trimellitic acid have a poisoning effect, i.e., they decrease the rate of oxidation when alkylaromatic compounds are oxidized to aromatic acids. This example is particularly pertinent because during a batch oxidation of pseudocumene there is a buildup of water in the reactor, since this is one of the by-products of the oxidation. Also near the end of the oxidation, there is an increase in the trimellitic acid concentration in the reactor. Both the water and the trimellitic acid will tend to deactivate the catalyst.

Table 2 illustrates the effect of chromium addition to the oxidation of pseudocumene; Table 3 illustrates the effect of molybdenum; and Table 4 illustrates the effect of tungsten. These three elements are in the same chemical family on the periodic table. It can be seen that molybdenum is unique in this chemical family in producing high rates of oxidation during the water and trimellitic acid additions. For example, in Table 3 in Example 9, the rate of oxidation was 0.77 ml dioxygen reacted/min with 20 percent water present in the reactor. However, this rate of oxidation is increased to 3.13 ml dioxygen reacted/min when 0.027 mmole of molybdenum is present (see Example 12 in Table 3). Table 3 further illustrates that increasing molybdenum content in the reactor first results in higher rates of oxidation but eventually decreased rates of oxidation even below the base case. We therefore have a very surprising result in that molybdenum can have either a strong activating effect or a strong poisoning effect depending upon its concentration. There is a optimum amount of molybdenum that gives maximum rates of oxidation.

Table 1 confirms the above results in a pilot plant. Thus, the oxidation in Table 1 was performed in a two-liter titanium-clad autoclave, equipped with a stirrer, internal cooling to control temperature, and inlets so that air and pseudocumene can be added during the oxidation. The vent gases were monitored for dioxygen and carbon dioxide content and were passed through traps to monitor pseudocumene, acetic acid, and water losses. The initial stage of the oxidation was operated semicontinuously where the pseudocumene was continuously pumped into the reactor at 150 psi air pressure and the temperature was slowly increased from 250° to 320° F. over a 25-minute time period. The oxidation was then completed by slowly increasing the pressure from 150 to 500 psi and the reactor temperature was slowly increased from 320° to 425° F. The reaction was terminated when the vent oxygen exceeded 18 percent.

Table 1 clearly illustrates the beneficial effect of molybdenum addition. In Table 1, Example 1 is a base case where no molybdenum was added. The desired trimellitic acid yield is only 59.6 percent. The pseudocumene was only partially oxidized to trimellitic acid as illustrated by the relatively high yield of intermediates. In the succeeding examples, increasing amounts of molybdenum were added into the reactor. The trimellitic yield increased from 59 percent with no molybdenum present to a maximum of 82 percent in Examples 4 and 5. Additional molybdenum addition in Example 16 resulted in reduced yield due mostly to excessive burning of the feedstock and acetic acid to carbon dioxide.

I have found that molybdenum overcomes the water-poisoning effect; see examples 10–15, 71, and 73 which contain molybdenum and examples 9, 70, and 72 which do not. Water is the product of the oxidation of any alkylaromatic compound. Molybdenum overcomes water poisoning in the oxidation of any alkylaromatic compound, i.e., toluene, ortho-xylene, meta-xylene, para-xylene, pseudocumene, 1,2,3-trimethylbenzene, 1,3,5-trimethylbenzene, durene, etc. Thus, the presence of molybdenum will result in higher rates of oxidation which, in practice, mean that lower concentrations of catalyst can be used; hence, advantageously, a less expensive and much more efficient oxidation process result.

During the batch oxidation of any hydrocarbon, aromatic acids eventually form and increase in concentration as the experiment proceeds. Tables 2–7 illustrate the effect of spiking an oxidation with various types of aromatic acids. I have shown in Tables 3 and 7 that phthalic acid, trimellitic acid, and hemimellitic acid deactivate the catalyst, but acetic, benzoic, isophthalic, and trimesic acids do not. In general, I found that aromatic acids containing two carboxylic acids ortho to each other on the aromatic ring deactivate the catalyst and decrease the rate of oxidation. Tables 3 and 7 also illustrate that molybdenum has the surprising ability to overcome the poisoning effect of aromatic acids such as phthalic, trimellitic, and hemimellitic. I have found that the oxidation of any alkylaromatic compound containing alkyl groups ortho to each other on the benzene ring benefit from molybdenum addition to the catalyst because aromatic acids will be formed which, in the absence of molybdenum, would poison the catalyst. Thus, for example, the oxidation of ortho-xylene, pseudocumene, 1,2,3-trimethylbenzene, durene, 1,2,3,4-tetramethylbenzene, and 1,2,3,5-tetramethylbenzene is aided by molybdenum addition since aromatic acids containing carboxylic acids ortho to each other are formed during the oxidation. Higher rates of oxidation occur with the presence of molybdenum which, in practice, results in lower catalyst concentrations and a less expensive oxidation process.

In the present invention for the oxidation of pseudocumene, the ratio of molybdenum to total conventional metal oxidation catalysts metals to bromine is in the range of about 0.10 to about 2.0 on a gram-atom basis. In our process in addition to molybdenum, cobalt, manganese, and bromine are utilized. The gram-atom ratio of molybdenum to cobalt is in the range of about 0.001 to about 1.0 and the ratio of cobalt to manganese is in the range of about 0.01 to about 100. My invention is also applicable to oxidations wherein in addition to manganese, zirconium is used in addition to cobalt.

Molybdenum can be added to the reaction in any form soluble in para-xylene, meta-xylene, ortho-xylene, pseudocumene, or 1,2,3-trimethylbenzene when it is being oxidized or in acetic acid when it is being used as reaction solvent. For example, molybdenum (VI) bis(2,4-pentanedionate) oxide can be used with manganese for the oxidation of para-xylene or meta-xylene in the presence of acetic acid or water and each of Mn and Co can be conveniently used as its acetate when para-xylene is oxidized in the presence of acetic acid solvent.

The source of molecular oxygen for the molybdenumenhanced oxidation of this invention can vary in $O_2$ content from that of air to oxygen gas. Air is the preferred source of molecular oxygen for oxidations conducted at temperatures of 100° C. and above, up to 250° C. The minimum pressure for such oxidations is that pressure which will maintain a substantial liquid phase of para-xylene or meta-xylene and 70–80 percent of the solvent. Suitable solvents include formic acid, acetic acid, propionic acid, n-butyric acid, isobutyric acid, n-valeric acid, trimethylacetic acid, and caproic acid, or water; the preferred solvent is acetic acid. Suitably, mixtures of water and the $C_1-C_6$ aliphatic acids can be utilized. It is essential that the molybdenum catalyst be soluble in the solvent. The solvent can amount to 1–10 parts on a weight basis per part of feedstock. The feedstock and solvent, such as acetic acid, not in the liquid phase because of vaporization by heat of reaction, are advantageously condensed and the condensate returned to the oxidation as a known means for removing heat and thereby temperature-controlling the exothermic oxidation reaction. Such vaporization of para-xylene or meta-xylene reactant and acetic acid solvent is also accompanied by vaporization of lower boiling by-product water.

The benefits to be derived from the use of molybdenum according to the present invention are indicated by results shown with respect to the following illustrative and comparative oxidations using pseudocumene as the methyl-substituted benzene to be oxidized.

After termination of the oxidations, the top of the reactor is removed and the total reactor effluents are collected. The resulting TRE products are submitted for aromatic acid analysis.

Product yields are calculated (and hereinafter reported) in mole percent of product per mole of feedstock charged.

Other pertinent details of the illustrative oxidations and the results so produced are presented hereinafter in Table 1. Representative sources of bromine include bromide, hydrogen bromide, sodium bromide, elemental bromine, benzyl bromide, tetrabromoethane, and others within the teachings of U.S. Pat. No. 2,833,816. Manganese is used as its acetate tetrahydrates and is preferred. The bromine source is hydrobromic acid. For the present novel catalyst system, the metal sources, Mo/Co and Mo/Co/Mn, can be any form of the metal which dissolves in the acetic acid or other $C_2-C_5$ aliphatic acid solvent. Also, the source of bromine can be those bromine compounds other than bromide salts of the metals in said system.

TABLE 1

| THE EFFECT OF MOLYBDENUM(VI) ADDITION IN PSEUDOCUMENE OXIDATIONS (FIRST STAGE SEMICONTINUOUS, SECOND STAGE BATCH[a]) | | | | | |
|---|---|---|---|---|---|
| | Example | | | | |
| | 1 | 2 | 3 | 4 | 5 |
| Lab book no. | 8363 | 8363 | 8363 | 8363 | 8363 |
| Page no. | 25 | 28 | 31 | 34 | 37 |

TABLE 1-continued
THE EFFECT OF MOLYBDENUM(VI) ADDITION IN PSEUDOCUMENE OXIDATIONS (FIRST STAGE SEMICONTINUOUS, SECOND STAGE BATCH[a])

| | Example | | | | |
|---|---|---|---|---|---|
| | 1 | 2 | 3 | 4 | 5 |
| Catalyst | | | | | |
| Cobalt, ppm | 900 | 900 | 900 | 900 | 900 |
| Mn/Co, mol/mol | 0.33 | 0.33 | 0.33 | 0.33 | 0.33 |
| (Co + Mn)/Br mol/basis | 1.07 | 1.07 | 1.07 | 1.07 | 1.07 |
| Solvent ratio[f] | 1.7 | 1.7 | 1.7 | 1.7 | 1.7 |
| Run time, min | 90 | 95 | 100 | 100 | 90 |
| Analysis of Cake Weight % | | | | | |
| TMLA[b] | 66.33 | 83.33 | 90.7 | 93.11 | 94.01 |
| Intermediates[c] | 7.75 | 6.32 | 0.64 | 0.63 | 0.56 |
| Low boilers[d] | 3.77 | 3.58 | 2.02 | 1.95 | 1.88 |
| High boilers[e] | 0.72 | 0.77 | 1.27 | 1.21 | 1.02 |
| Mass Accountability | 76.29 | 88.96 | 89.73 | 92.19 | 92.16 |
| Yield, Mol % | | | | | |
| TMLA, obs. | 59.65 | 73.44 | 78.84 | 81.68 | 81.18 |
| $CO_x$ | 4 | 4.73 | 6.88 | 6.62 | 7.44 |
| Activator | None | Mo | Mo | Mo | Mo |
| Activator/Co, mol/mol | 0.0 | 0.009 | 0.045 | 0.14 | 0.27 |
| Final reactor Temp., °F. | 425 | 425 | 425 | 425 | 425 |

[a]Each run is performed starting with 15.0 g pseudocumene, 399 g acetic acid, 21 g water, 1.85 g cobalt(II) acetate tetrahydrate, 0.607 g manganese(II) acetate tetrahydrate, and 1.56 g 48 percent aqueous hydrobromic acid. Upon initiation of oxidation at 150 psi pressure and 262° F. with air feed, 500 g of pseudocumene is pumped into the reactor at 20 g/min. The temperature and pressure are then slowly increased during the oxidation to a final temperature given in the table and a pressure of 400 psi. Molybdenum is added as molybdenum(VI) oxide bis(2,4-pentanedionate). Oxidations are terminated when the vent oxygen concentrations reach 18 percent.
[b]Trimellitic acid.
[c]Sum of methyldicarboxylic aromatic compounds.
[d]Sum of benzoic and phthalic acids.
[e]A number of these are detected. The majority of these are tetracarboxybenzenes.
[f]Weight of acetic acid divided by weight of pseudocumene.

TABLE 2
THE EFFECT OF CHROMIUM ON THE RATE OF A Co/Mn/Br CATALYZED OXIDATION OF PSEUDOCUMENE[1,2]

| | Example | | |
|---|---|---|---|
| | 6 | 7 | 8 |
| Oxidation Run Number | 7233-66 | 7233-74 | 8692-60 |
| Chromium present, mmole[3] | 0.0 | 0.4 | 4.0 |
| Oxidation rate, ml oxygen reacted/min | | | |
| 0.3% water present | 6.66 | 7.12 | 5.14 |
| 5.0% water present | 5.64 | 5.96 | 5.03 |
| 13% water present | 4.33 | 2.67 | 2.92 |
| 20% water present | 1.43 | 0.92 | 1.20 |
| 20% water + 24 mmole trimellitic acid[4] | 0.77 | 0.62 | 0.93 |
| 20% water + 48 mmole trimellitic acid | 0.10 | 0.21 | 0.21 |
| 20% water + 71 mmole trimellitic acid | 0.0 | 0.10 | 0.05 |
| 20% water + 95 mmole trimellitic acid | 0.0 | 0.0 | 0.05 |

[1]Pseudocumene is 1,2,4-trimethylbenzene.
[2]Reactions are run in glass reactor containing 2.01 mmole cobalt(II) acetate tetrahydrate, 2.01 mmole manganese(II) acetate tetrahydrate, 4.0 mmole sodium bromide, 10.0 ml pseudocumene, and 100.0 ml acetic acid. The source of oxygen is air which is passed through a glass frit at the bottom of the reactor at a rate of 52 ml/min. The vent oxygen concentration is constantly measured using a Beckman oxygen analyzer. The rate of oxygen uptake is calculated from the vent oxygen concentration and the flow rate of air through the reactor. The temperature is maintained at 95° C. and the pressure is atmospheric. Water and trimellitic acid are sequentially added in the amounts indicated on the table.
[3]Chromium is added as the chromium(III) acetate.
[4]Trimellitic acid is 1,2,4-tricarboxybenzene.

TABLE 3
THE EFFECT OF MOLYBDENUM ON THE RATE OF A Co/Mn/Br CATALYZED OXIDATION OF PSEUDOCUMENE[1]

| | Example | | | | | | | |
|---|---|---|---|---|---|---|---|---|
| | 9 | 10 | 11 | 12 | 13 | 14 | 15 | 16 |
| Oxidation Run Number | 7233-66 | 8021-56 | 8021-104 | 8021-68 | 8021-28 | 8021-70 | 8021-26 | 8022-108 |
| Molybdenum addn, mmole[2] | 0.0 | 0.0089 | 0.013 | 0.027 | 0.027 | 0.053 | 0.080 | 0.400 |
| Oxidation rate, ml oxygen reacted/min | | | | | | | | |
| 0.3% water present | 6.66 | 6.46 | 6.10 | 6.82 | 6.82 | 6.94 | 6.58 | 0.26 |
| 5.0% water present | 5.64 | 5.37 | 5.03 | 5.61 | 5.72 | 5.78 | 5.55 | 0.05 |
| 13% water present | 4.33 | 5.14 | 4.97 | 5.84 | 5.90 | 5.96 | 5.20 | 0.0 |
| 20% water present | 1.43 | 2.75 | 3.01 | 3.13 | 3.02 | 3.13 | 2.96 | 0.0 |
| 20% water + 24 mmole trimellitic acid | 0.77 | 3.90 | 4.48 | 3.13 | 4.70 | 4.99 | 3.90 | 0.0 |
| 20% water + 48 mmole trimellitic acid | 0.10 | 0.26 | 4.48 | 4.70 | 5.05 | 5.28 | 3.02 | 0.0 |
| 20% water + 71 mmole trimellitic acid | 0.0 | 0.10 | 3.01 | 4.99 | 4.87 | 4.41 | 0.10 | 0.0 |
| 20% water + 95 mmole trimellitic acid | 0.0 | 0.0 | 0.10 | 0.10 | 3.24 | 0.10 | 0.05 | 0.0 |

[1]Conditions and apparatus are identical to those described in Table 2.
[2]Molybdenum is added as molybdenum(VI) oxide bis(2,4-pentanedionate).

TABLE 4
THE EFFECT OF TUNGSTEN ON THE RATE OF A Co/Mn/Br CATALYZED OXIDATION OF PSEUDOCUMENE[1]

| | Example | | | |
|---|---|---|---|---|
| | 17 | 18 | 19 | 20 |
| Oxidation Run Number | 7233-66 | 7233-66 | 8021-64 | 7233-72 |
| Tungsten addn, mmole[2] | 0.0 | 0.016 | 0.080 | 0.40 |
| Oxidation rate, ml oxygen reacted/min | | | | |
| 0.3% water present | 6.66 | 6.28 | 6.16 | 5.17 |
| 5.0% water present | 5.64 | 5.14 | 4.97 | 4.60 |
| 13% water present | 4.33 | 4.68 | 4.29 | 2.35 |

TABLE 4-continued

THE EFFECT OF TUNGSTEN ON THE RATE OF A Co/Mn/Br CATALYZED OXIDATION OF PSEUDOCUMENE[1]

| | Example | | | |
|---|---|---|---|---|
| | 17 | 18 | 19 | 20 |
| 20% water present | 1.43 | 1.08 | 1.59 | 1.61 |
| 20% water + 24 mmole trimellitic acid | 0.77 | 1.11 | 1.06 | 1.41 |
| 20% water + 48 mmole trimellitic acid | 0.1 | 0.16 | 0.16 | 1.23 |
| 20% water + 71 mmole trimellitic acid | 0.0 | 0.1 | 0.1 | 0.90 |
| 20% water + 95 mmole trimellitic acid | 0.0 | 0.1 | 0.1 | 0.05 |

[1]Conditions and appratus identical to those described in Table 2.
[2]Tungsten added as tungsten(VI) oxide.

TABLE 5

Effect of the Addition of Selected Acids on the Rate of Pseudocumene Oxidations[a]
Acetic Acid Solvent Contains 20% Water

| Example | Acid | Oxidation Run Number | (Acid) Conc. M | Rate, ml $O_2$/min Before Addn. | After Addn. | % Change |
|---|---|---|---|---|---|---|
| 16 | Acetic Acid | 7233-16 | 0.19 | 1.45 | 1.66 | 14 |
| 17 | | 7233-16 | 0.37 | 1.45 | 1.75 | 21 |
| 18 | | 7233-16 | 0.56 | 1.45 | 1.97 | 36 |
| 19 | | 7233-16 | 0.75 | 1.45 | 2.13 | 47 |
| 20 | Benzoic Acid | 6931-168 | 0.14 | 1.32 | 1.64 | 24 |
| 21 | | 6931-168 | 0.38 | 1.32 | 1.84 | 39 |
| 22 | | 6931-168 | 0.57 | 1.32 | 1.78 | 35 |
| 23 | | 6931-168 | 0.76 | 1.32 | 1.84 | 39 |
| 24 | Isophthalic Acid | 7233-5 | 0.19 | 1.36 | 1.66 | 22 |
| 25 | | 7233-7 | 0.12 | 1.71 | 1.95 | 14 |
| 26 | | 8021-174 | 0.19 | 1.22 | 1.48 | 21 |
| 27 | | 7232-124 | 0.19 | 1.64 | 1.43 | −13 |
| 28 | | 7232-124 | 0.38 | 1.64 | 0.30 | −82 |
| 29 | | 7232-124 | 0.57 | 1.64 | 0.15 | −91 |
| 30 | | 7232-124 | 0.76 | 1.64 | 0.05 | −97 |
| 31 | Phthalic Acid | 6931-166 | 0.19 | 1.03 | 0.99 | −4 |
| 32 | | 6931-166 | 0.38 | 1.03 | 0.67 | −35 |
| 33 | | 6931-166 | 0.57 | 1.03 | 0.14 | −86 |
| 34 | | 6931-166 | 0.76 | 1.03 | 0.05 | −95 |
| 35 | | 8022-182 | 0.19 | 1.22 | 0.56 | −54 |
| 36 | | 8022-182 | 0.38 | 1.22 | 0.10 | −92 |
| 37 | | 8022-182 | 0.57 | 1.22 | 0.05 | −96 |
| 38 | | 8022-182 | 0.76 | 1.22 | 0.05 | −96 |
| 39 | Trimesic Acid | 7232-102 | 0.19 | 1.50 | 1.90[b] | 27 |
| 40 | Hemimellitic Acid | 7233-166 | 0.038 | 1.27 | 0.10 | −92 |
| 41 | | 7233-166 | 0.076 | 1.27 | 0.05 | −96 |
| 42 | | 7233-192 | 0.038 | 1.32 | 0.31 | −76 |
| 43 | | 7233-192 | 0.076 | 1.32 | 0.05 | −96 |
| 44 | | 7233-192 | 0.190 | 1.32 | 0.05 | −96 |
| 45 | | 7233-192 | 0.380 | 1.32 | 0.00 | −100 |

[a]Initial conditions are identical to Table 2.
[b]Solubility of aromatic acid is exceeded.

TABLE 6

Effect of the Addition of Selected Acids on the Rate of Pseudocumene Oxidation[a,b]
Acetic Acid Solvent Contains 10% Water

| Example | Acid | Oxidation Number | (Acid) M | Rate, ml $O_2$/min Before Addn. | After Addn. | % Change |
|---|---|---|---|---|---|---|
| 46 | Benzoic Acid | 7232-80 | 0.037 | 3.5 | 4.6 | 29 |
| 47 | | 7232-80 | 0.11 | 3.5 | 4.7 | 32 |
| 48 | | 7232-80 | 0.26 | 3.5 | 4.9 | 29 |
| 49 | | 7232-80 | 0.55 | 3.5 | 4.7 | 32 |
| 50 | Isophthalic Acid | 7233-118 | 0.037 | 5.0 | 6.2 | 30 |
| 51 | | 7233-118 | 0.11 | 5.0 | 6.1 | 35 |
| 52 | | 7233-76 | 0.037 | 3.7 | 5.0 | 33 |
| 53 | | 7233-76 | 0.11 | 3.7 | 4.9 | 30 |
| 54 | Phthalic Acid | 7233-116 | 0.037 | 4.6 | 6.2 | 35 |
| 55 | | 7233-116 | 0.037 | 4.6 | 5.0 | 8 |
| 56 | | 7233-116 | 0.26 | 4.6 | 6.1 | 32 |
| 57 | | 7233-116 | 0.55 | 4.6 | 6.1 | 32 |
| 58 | | 7232-120 | 0.037 | 4.6 | 6.0 | 30 |
| 59 | | 7232-120 | 0.11 | 4.6 | 5.8 | 27 |
| 60 | | 7232-120 | 0.26 | 4.6 | 6.0 | 30 |
| 61 | | 7232-120 | 0.55 | 4.6 | 6.2 | 35 |
| 62 | Trimellitic | 7232-74 | 0.037 | 4.7 | 4.9 | 4 |

TABLE 6-continued

Effect of the Addition of Selected
Acids on the Rate of Pseudocumene Oxidation[a,b]
Acetic Acid Solvent Contains 10% Water

| Example | Acid | Oxidation Number | (Acid) M | Rate, ml O₂/min Before Addn. | Rate, ml O₂/min After Addn. | % Change |
|---|---|---|---|---|---|---|
| 63 | Acid | 7232-74 | 0.11 | 4.7 | 3.7 | −20 |
| 64 | Hemimellitic | 7232-84 | 0.037 | 4.5 | 5.4 | 21 |
| 65 | Acid | 7232-84 | 0.11 | 4.5 | 3.9 | −13 |
| 66 | | 7232-84 | 0.26 | 4.5 | 2.1 | −52 |
| 67 | | 7232-84 | 0.55 | 4.5 | 0.0 | −100 |
| 68 | Trimesic Acid | 7232-82 | 0.037 | 4.5 | 6.1 | 35 |
| 69 | | 7232-82 | 0.11 | 4.5 | 5.8 | 30 |

[a] Separate experiments are performed under identical conditions to insure that the solubility of the aromatic is not exceeded.
[b] Initial conditions are identical to Table 2.

TABLE 7

The Effect of Molybdenum on the Rate of a
Co/Mn/Br Catalyzed Oxidation of Pseudocumene[1]

| | Example 70 | 71 | 72 | 73 |
|---|---|---|---|---|
| Oxidation Run No. | 10290-28 | 10290-34 | 10290-31 | 10290-38 |
| Molybdenum Addition, mmole[2] | 0.0 | 0.027 | 0.0 | 0.027 |
| Aromatic Acid | Phthalic[3] | Phthalic[3] | Hemimellitic[4] | Hemimellitic[4] |
| Oxidation Rate, ml Oxygen Reacted/Min | | | | |
| 0.3% water present | 6.35 | 6.61 | 6.22 | 7.03 |
| 5.0% water present | 5.91 | 5.97 | 5.59 | 6.15 |
| 13% water present | 3.87 | 5.10 | 4.11 | 5.18 |
| 20% water present | 1.26 | 2.66 | 1.38 | 2.76 |
| 20% water + aromatic acid | 0.66 | 3.06 | 0.36 | 2.70 |
| 20% water + aromatic acid | 0.15 | 3.16 | 0.05 | 2.36 |
| 20% water + aromatic acid | 0.15 | 2.86 | 0.0 | 1.47 |
| 20% water + aromatic acid | 0.25 | 2.18 | 0.0 | 0.0 |

[1] Conditions and apparatus are identical to those described in Table 2.
[2] Molybdenum is added as molybdenum(VI) oxide bis(2,4-pentanedionate).
[3] 24 mmole phthalic acid are added at each addition.
[4] 4.76, 4.76, 4.76, and 9.52 mmole of hemimellitic acid are added upon successive additions.

I claim:

1. A process for oxidizing polymethylbenzenes with molecular oxygen to benzene polycarboxylic acids under liquid-phase conditions wherein the process comprises conducting the oxidation in the presence of $C_{1-6}$ aliphatic carboxylic acid or a mixture of a $C_{1-6}$ aliphatic acid and water, wherein the carboxylic acid is a solvent for the reaction and also for a cobalt-molybdenum-manganese-bromine catalyst, at temperatures in the range of about 100° to about 250° C. in the presence of a catalyst system consisting essentially of a source of bromine, cobalt, molybdenum, and manganese wherein molybdenum is an effective promoter for the cobalt-manganese-bromine catalyst system and wherein the gram-atom ratio of molybdenum to cobalt is in the range of about 0.001 to about 1.0 and the ratio of cobalt to manganese is in the range of about 0.01 to about 100.

2. The process of claim 1 wherein p-xylene is oxidized to terephthalic acid.

3. The process of claim 1 wherein o-xylene is oxidized to o-phthalic acid.

4. The process of claim 1 wherein pseudocumene is oxidized to trimellitic acid.

5. The process of claim 1 wherein m-xylene is oxidized to isophthalic acid.

6. The process of claim 1 wherein durene is oxidized to pyromellitic acid.

7. A process for oxidizing pseudocumene with molecular oxygen to trimellitic acid under liquid-phase conditions wherein the process comprises conducting the oxidation in the presence of acetic acid at temperatures in the range of about 100° to about 250° C. in the presence of a catalyst system consisting essentially of a source of bromine, manganese, cobalt, and molybdenum wherein the molybdenum is soluble in acetic acid and the gram-atom ratio of molybdenum to cobalt is in the range of about 0.001 to about 1.0 and the ratio of cobalt to manganese is in the range of about 0.01 to about 100.

8. A process for oxidizing polymethylbenzenes with molecular oxygen to benzene polycarboxylic acids under liquid-phase conditions wherein the process comprises conducting the oxidation in the presence of $C_1-C_6$ aliphatic carboxylic acid or a mixture of a $C_{1-6}$ aliphatic acid and water, wherein the carboxylic acid is a solvent for the reaction and also for a cobalt-molybdenum-zirconium-manganese-bromine catalyst, at temperatures in the range of about 100° to about 250° C. in the presence of a catalyst system consisting essentially of a source of bromine, cobalt, molybdenum, zirconium, and manganese wherein molybdenum is an effective promoter for the cobalt-manganese-bromine catalyst system and wherein the gram-atom ratio of molybdenum to cobalt is in the range of about 0.001 to about 1.0 and the ratio of cobalt to manganese is in the range of about 0.01 to about 100.

* * * * *